United States Patent [19]

Siu-Ming

[11] Patent Number: 5,006,557
[45] Date of Patent: Apr. 9, 1991

[54] ACNE SOLUTION

[76] Inventor: Yee Siu-Ming, N. 52, Lane 172, Kuang Tong Rd., Ping Tong City, Taiwan

[21] Appl. No.: 511,366

[22] Filed: Apr. 19, 1990

[51] Int. Cl.$^5$ .......................... A61K 7/48; A61K 9/08; A61K 31/19
[52] U.S. Cl. ...................................... 514/557; 514/859
[58] Field of Search .................................. 514/557, 859

[56] References Cited

U.S. PATENT DOCUMENTS

| | | | |
|---|---|---|---|
| 2,590,856 | 4/1952 | Greenspan et al. | 514/557 |
| 3,026,247 | 3/1962 | Hill | 514/557 |
| 4,032,628 | 6/1977 | Papantoniou et al. | 514/939 |
| 4,105,782 | 8/1978 | Yu et al. | 514/557 |
| 4,196,204 | 1/1980 | Petzoldt et al. | 514/178 |
| 4,197,316 | 4/1980 | Yu et al. | 514/557 |
| 4,224,319 | 9/1980 | Marcadet | 514/171 |
| 4,234,599 | 11/1980 | Van Scott et al. | 514/557 |
| 4,244,948 | 1/1981 | Boghosian et al. | 514/859 |
| 4,292,326 | 9/1981 | Nazzaro-Purro | 514/859 |
| 4,361,584 | 11/1982 | Fulton | 514/859 |
| 4,363,815 | 12/1982 | Yu et al. | 514/557 |
| 4,406,884 | 9/1983 | Fanzi et al. | 514/557 |
| 4,424,234 | 1/1984 | Alderson et al. | 514/557 |
| 4,512,985 | 4/1985 | Maignan et al. | 514/859 |
| 4,608,370 | 8/1986 | Aronsohn | 514/557 |
| 4,746,674 | 5/1988 | Pierpaoli et al. | 514/859 |
| 4,895,727 | 1/1990 | Allen | 514/946 |

FOREIGN PATENT DOCUMENTS 60-152415  8/1985  Japan ..................................... 514/859

Primary Examiner—Shep K. Rose
Attorney, Agent, or Firm—Browdy and Neimark

[57] ABSTRACT

The present invention is related to Acne treatment. Acne is considered as an inflammatory disease which is of common. A solution formed of Acetic Acid Glacial, Almond Essence, Glycerine, and water is proposed, and testing results are suggesting the merits thereof.

1 Claim, No Drawings

ACNE SOLUTION

SUMMARY OF THE INVENTION

The conventional methods of treatment may be categorized into three folds, they are
1. Clinical treatment, it shows that current practice is still not able to fully control ACNE by medical profession while relevent literature also reaches the same conclusion.
2. Cosmetical treatment, somehow, has its own theory and performed by trained personnel, and normally this inflammatory disease is treated by pressing at where the Acne is, then apply some Antibiotics to prevent infection. Somehow, this process takes a long time and is painful during treatment.
3. Self-treatment, there are numerous kinds of liquid or cream like medicines are produced and proposed to cure Acne, nevertheless, it is observed that the healing process is too long.

therefore, it is an object to provide a means provided with relatively fast in timing and less in pain.

The present invention, therefore, relates to an novel discovery of Acne treatment which is characterized by using one Acetic Acid Glacial, three Almond Essence, one Glycerine mixture and nine water solution in terms of proportion of ingredients.

The present invention also relies on Acetic Acid Glacial being able to immerse into expidermis layer of wellknown skin structure and kill certain kinds of bacterias being seen thereon; Glycerine being able to prevent drying of skin upon applying said. Acetic Acid Glacial; Almond Essence being able to cover the bad smell of Acetic Acid Glacial; and Water to prevent harm done by to the skin Acetic Acid Glacial.

It is also to be understood that the ingredients of the present invention can be identified by volume, that is

| Acetic Acid Glacial | 6.25% |
| Almond Essence | 18.75% |
| Glycerine | 18.75% |
| Water | 56.25% | to compose of a solution of the kind to heal Acne.

As applying this solution, one can use any of clean absorbing means to seep one drop of said solution, then apply on the surface of skin needed to be treated. It is observed that one drop is required a day. After continuing for a few days ACNE may disappear.

Conclusively, with applying solution of the kind mentioned, ACNE may be healed with following additional advantages.
1. The treatment is safe, no side-effect is observed since all the ingredients are well known matters.
2. Solution of this kind dry quickly to prevent possible damage to clothes (to make clothes dirty).
3. The treatment is simple and safe, and is economical since all ingredients are easily obtained.

DETAIL DESCRIPTION OF THE PRESENT INVENTION

The present invention can be further described thereafter.

The solution of the kind referred to is comprising one Acetic Acid Glacial, three Almond Essence, three Glycerine and Nine Water proportionally. After mixing these ingredients, a bottle or the like is prepared with a cover to prevent vaporizing.

A number of volunteers were treated under full control and observation, after three days treatment, all Acnes were disappearing.

It is a well-known fact that Acne is occurred under epidermis and on dermis of skin structure. It is also known that Acetic Acid Glacial is able to penetrate into skin till dermis and to kill numerous kinds of bacteria. By utilizing these properties, however, Acne may be healed more effective with less pain and with help of Almond essence to eliminate bad smell of Acetic Acid Glacial, Glycerine to prevent skin drying out as applying Acetic Acid Glacial, and water to make Acetic Acid Glacial less strong.

I claim:

1. An acne treating solution consisting essentially of Acetic Acid Glacial 6.25%
Almond Essence 18.75%
Glycerine 18.75%
and Water 56.25%.

* * * * *